United States Patent [19]

Horn et al.

[11] 4,248,781

[45] Feb. 3, 1981

[54] PURIFICATION OF CRUDE CAPROLACTAM

[75] Inventors: Peter Horn, Hirschberg; Hugo Fuchs, Ludwigshafen, both of Fed. Rep. of Germany

[73] Assignee: BASF Aktiengesellschaft, Fed. Rep. of Germany

[21] Appl. No.: 78,028

[22] Filed: Sep. 24, 1979

[30] Foreign Application Priority Data

Oct. 17, 1978 [DE] Fed. Rep. of Germany ....... 2845075

[51] Int. Cl.³ .......................................... C07D 201/16
[52] U.S. Cl. .............................................. 260/239.3 A
[58] Field of Search ................................. 260/239.3 A

[56] References Cited

U.S. PATENT DOCUMENTS

| 2,813,858 | 11/1957 | Joris | 260/239.3 A |
| 3,476,744 | 11/1969 | Berther | 260/239.3 A |

FOREIGN PATENT DOCUMENTS

| 1055537 | 4/1959 | Fed. Rep. of Germany | 260/239.3 A |
| 2641478 | 5/1977 | Fed. Rep. of Germany | 260/239.3 A |
| 2550934 | 5/1977 | Fed. Rep. of Germany | 260/239.3 A |
| 1529559 | 10/1978 | United Kingdom | 260/239.3 A |
| 1530357 | 10/1978 | United Kingdom | 260/239.3 A |

Primary Examiner—Henry R. Jiles
Assistant Examiner—Robert T. Bond
Attorney, Agent, or Firm—Keil & Witherspoon

[57] ABSTRACT

A process for purifying crude caprolactam which has been obtained by rearrangement of cyclohexanone-oxime in the gas phase over a catalyst containing boron trioxide, wherein caprolactam is crystallized out, by cooling, from a melt which contains, per 100 parts by weight of crude caprolactam, from 5 to 30 parts by weight of primary alkanols or fatty acids which have a carbon chain of 6 to 10 carbon atoms and are substituted by alkyl radicals of 1 to 5 carbon atoms, and from 0 to 5 parts by weight of water, and is separated from the mother liquor.

5 Claims, No Drawings

PURIFICATION OF CRUDE CAPROLACTAM

The present invention relates to a process for purifying crude caprolactam which has been obtained by rearrangement of cyclohexanone-oxime in the gas phase over a catalyst containing boron trioxide.

Caprolactam which has been produced by rearrangement in the gas phase over a catalyst containing boron trioxide contains, as impurities, not only from 0.05 to 5 mole % of boric acid but also a number of other contaminants of unknown chemical composition. These contaminants are distinguished by an unpleasant odor and cause the caprolactam to have a high absorption in the ultraviolet region. Both properties are undesirable. German Laid-Open Application DOS No. 2,550,934 proposes that catalytically produced caprolactam be purified by treatment with a base in the presence of toluene and water. This results in 3 layers which must be separated from one another. Apart from the fact that it is not clear from this how the UV number can be lowered, the separation of 3 phases is technically very troublesome. Further, German Laid-Open Application DOS No. 2,641,478 discloses a process for purifying caprolactam obtained by gas-phase rearrangement, in which the crude caprolactam is treated with potassium permanganate in the presence of water and subsequently recrystallized from a solvent. The treatment with potassium permanganate is troublesome inasmuch as the manganese dioxide which separates out is not easy to remove.

It is an object of the present invention to provide a simple, technically not troublesome process in which it is possible to remove the impurities which are responsible for the unpleasant odor and the high UV number at the same time as removing the boric acid contained in the product.

We have found that this object is achieved by a process for purifying crude caprolactam which has been obtained by rearrangement of cyclohexanone-oxime in the gas phase over a catalyst containing boron trioxide, wherein caprolactam is crystallized out, by cooling, from a melt which contains, per 100 parts by weight of crude caprolactam, from 5 to 30 parts of weight of primary alkanols or fatty acids which have a carbon chain of 6 to 10 carbon atoms and are substituted by alkyl radicals of 1 to 5 carbon atoms, and from 0 to 5 parts by weight of water, and is separated from the mother liquor.

The novel process has the advantage of being technically simple to carry out and that impurities which are responsibe for the unpleasant odor and the high UV number are effectively and simply removed.

Crude caprolactam which is used as the starting material for the purification according to the invention is obtained, for example, by the process described in German Published Application DAS No. 1,055,537, wherein caprolactam is separated out from vapors, containing caprolactam, by means of water in countercurrent in a column. The purification operation starts from a melt which contains, per 100 parts by weight of crude caprolactam, from 5 to 30 parts by weight of primary alkanols or fatty acids which have a carbon chain of 6 to 10 carbon atoms and are substituted by alkyl radicals of 1 to 5 carbon atoms. Examples of suitable compounds are 2-ethyl-hexan-1-ol, isononanol and isodecanol, as well as 2-ethylhexanoic acid. Primary alkanols having the stated number of carbon atoms, in particular 2-ethyl-hexan-1-ol, have proved especially suitable. In addition, the melt contains from 0 to 5, especially from 1 to 4, parts by weight of water per 100 parts by weight of crude caprolactam. The melt is prepared, for example, by adding the said components to molten crude caprolactam or by melting solid caprolactam together with the said components. A melt of this type, comprising 100 parts by weight of crude caprolactam, 17.6 parts by weight of 2-ethyl-hexan-1-ol and 3.1 parts by weight of water solidifies, for example, at 55° C.

Caprolactam is crystallized out of the melt, described above, by cooling. Advantageously, the melt is cooled to from 10° to 30° C., especially from 15° to 25° C. The crystallization is carried out in conventional industrial crystallization equipment, as described, for example, in "Grundoperation Chemischer Verfahrenstechnik" by W. R. A. Vauk and H. A. Müller, Verlag Theodor Steinkopff, Dresden and Leipzig, 1966, 2nd edition, pages 528–535, in the chapter on "Crystallizers". The caprolactam which as crystallized out is then separated from the mother liquor, for example by decanting or especially by centrifuging.

Depending on the content of impurities, a single purification operation may suffice; alternatively, if necessary, the purification operation according to the invention can be repeated several times. Advantageously, the caprolactam contained in the mother liquor is recovered from the latter by distillation and is recycled to the crude caprolactam. The alkanols and carboxylic acids also recovered are also re-used for the purification operation.

The impurities are discharged as a residue.

The caprolactam purified according to the process of the invention is advantageously then distilled once before being used further.

Caprolactam may be used for the preparation of nylons.

The process according to the invention is illustrated by the Examples which follow.

EXAMPLE 1

A melt of 100 parts by weight of crude caprolactam having a UV number of 16,000, 17.6 parts by weight of 2-ethylhexan-1-ol and 3.1 parts by weight of water is cooled to 20° C. whilst stirring and the slurry is centrifuged. The caprolactam which has crystallized (73.6 parts by weight) has a UV number of 1,758. A melt of this caprolactam and 17.6 parts by weight of 2-ethylhexan-1-ol is again crystallized, and centrifuged. The crystalline product obtained consists of 56.5 parts by weight of caprolactam having a UV number of 132. Distillation of the mother liquors gives 34 parts by weight of 2-ethylhexanol, 37 parts by weight of caprolactam (UV number 7,100), 3.1 parts by weight of water and 6.2 parts by weight of residue.

EXAMPLE 2

A melt of 69 parts by weight of crude caprolactam having a UV number of 16,000, 31 parts by weight of caprolactam from the mother liquor of Example 1 (UV number 7,100), 17.6 parts by weight of 2-ethylhexan-1ol and 3.1 parts by weight of water is cooled to 20° C. whilst stirring, and crystalline caprolactam is obtained from the slurry by centrifuging. The crystalline caprolactam (70.7 parts by weight) has a UV number of 1,287. A melt of this caprolactam (70 parts by weight) and 17.6 parts by weight of 2-ethylhexanol is again crystallized and centrifuged. Caprolactam (51.2 parts by weight)

having a UV number of 70 is obtained as the crystalline product. Distillation of this product gives caprolactam of the following quality:

| | |
|---|---|
| Solidification point (°C.) | 69.05 |
| pH | 7.13 |
| Content of volatile bases | 0.38 milliequivalent/mg |
| Permanganate absorption number | 8.6 |
| UV number | 11.5 |

The extinction is determined from the light transmission of a 1 percent strength caprolactam solution in water (50 ml or 100 ml of solution) after adding 0.01 N KMnO$_4$ solution (1 or 2 ml) at 25° C., the measurement being made against an identical solution without caprolactam after 600 seconds.

UV number

Principle:

The absorption of the caprolactam is measured in the spectral region from 360 to 270 nm and is expressed as a figure of merit after appropriate conversion.

Analytical instruments:

1 recording single-beam spectrophotometer (Carl Zeiss DMR/21), 1 Erlenmeyer flask (200 ml), 2 quartz cells, 10 cm long (layer thickness 10 cm), with cover.

Instructions:

50 mg of caprolactam are dissolved in 50 g of cold doubly distilled water in an Erlenmeyer flask. A cell is filled with this solution up to the calibration mark. The second cell is filled with the same doubly distilled water and represents the comparative solution.

Both cells are now closed with their lids, the ground surfaces are cleaned with tissue paper, and the cells are inserted in the cell holder. The spectrum is then recorded from 370 nm to 260 nm in accordance with the instrument operating manual. The rate of recording is 50 (units). The extinction measurement is effected in the 0-1 measuring range.

When the recording has been completed, a mark is made on the paper at intervals of 10 nm from 270 to 360 nm.

Evaluation:

The extinctions are read off the diagram at 270, 280, 290, 300, 310, 320, 330, 340, 350 and 360 nm, and are added.

The sum of the 10 extinction values is multiplied by 2 and gives the UV number. Accordingly, the UV number is always based on 100% strength caprolactam and on a layer thickness of 10 cm.

We claim:

1. A process for purifying crude caprolactam which has been obtained by rearrangement of cyclohexanone-oxime in the gas phase over a catalyst containing boron trioxide, wherein caprolactam is crystallized out, by cooling, from a melt which contains, per 100 parts by weight of crude caprolactam, from 5 to 30 parts by weight of primary alkanols or fatty acids, each of which have a carbon chain of 6 to 10 carbon atoms and are substituted by alkyl radicals of 1 to 5 carbon atoms, and from 0 to 5 parts by weight of water, and is separated from the mother liquor.

2. A process as claimed in claim 1, wherein the melt is cooled to from 10° to 30° C.

3. A process as claimed in claim 1 or 2, wherein 2-ethylhexan-1-ol is used.

4. A process as claimed in claim 3 wherein said melt additionally contains water in the amount of 1 to 4 parts by weight per 100 parts by weight of the crude caprolactam.

5. A process as claimed in claim 1 wherein said melt additionally contains water in the amount of 1 to 4 parts by weight per 100 parts by weight of the crude caprolactam.

* * * * *